United States Patent [19]

Laborit et al.

[11] Patent Number: 5,322,840
[45] Date of Patent: Jun. 21, 1994

[54] TREATMENT OF HYPERLIPEMIA AND HYPERTRIGLYCERIDEMIA

[75] Inventors: Geneviève Laborit, Paris; Camille Wermuth, Strasbourg, both of France

[73] Assignee: Centre d'Etudes Experimentales et Cliniques de Physiobiologie, de Pharmacologie et d'Eutonologie (Cepbepe), France

[21] Appl. No.: 988,017

[22] Filed: Dec. 9, 1992

Related U.S. Application Data

[63] Continuation of Ser. No. 739,860, Aug. 2, 1991, abandoned.

[30] Foreign Application Priority Data

Aug. 3, 1990 [FR] France ................... 90 09957

[51] Int. Cl.$^5$ .................... A61K 31/70; C07H 19/067
[52] U.S. Cl. ........................ 514/46; 536/27.62
[58] Field of Search .............. 514/46; 536/27.62

[56] References Cited

U.S. PATENT DOCUMENTS 4,906,620 4/1993 Laborit et al. ................ 514/46

FOREIGN PATENT DOCUMENTS

| 0186574 | 7/1986 | European Pat. Off. | 514/46 |
| 322242 | 6/1989 | European Pat. Off. | 514/46 |
| 2406587 | 8/1975 | Fed. Rep. of Germany | 514/46 |
| 2111862 | 6/1972 | France | 514/46 |
| 2239252 | 2/1975 | France | 514/46 |
| 2077725 | 12/1981 | United Kingdom | 514/46 |

OTHER PUBLICATIONS

Bonifacj et al., "Action of N$^6$-(amido-3-propyl) adenosine hydrochloride (Agr 529) on Plasma Corticosterone Levels in Rats," *Res. Comm. Chem. Pathol. Pharmacol.,* 68(3), 299–305 (1990); Medline Abstract 07442911, File 155, Dialog Info. Serv.); Only abstract supplied.
Laborit et al., "Changes in Plasma Cathecholamine Levels After the Intraperitoneal and Intracerebroventicular Administration of Adenosine Analogs and of Clonidine in Conscious Rats," *Res. Comm. Chem. Pathol. Pharmacol.,* 68(3), 307–327 (1990); Medline Abstract 07442912, File 155, Dialog Info. Serv.); Only abstract supplied.

*Primary Examiner*—Johnnie R. Brown
*Assistant Examiner*—L. Eric Crane
*Attorney, Agent, or Firm*—Rosenman & Colin

[57] ABSTRACT

The object of the present invention is the administration of a substance which contains, as active principle, an adenosine substituted on N$^6$ of formula I in which $R_1, R_2$ and $R_3$ each represents hydrogen or $$CH_3-CH_2-\overset{\overset{O}{\|}}{C}-$$

for the treatment of hyperlipemia and/or hypertriglyceridemia.

6 Claims, 8 Drawing Sheets

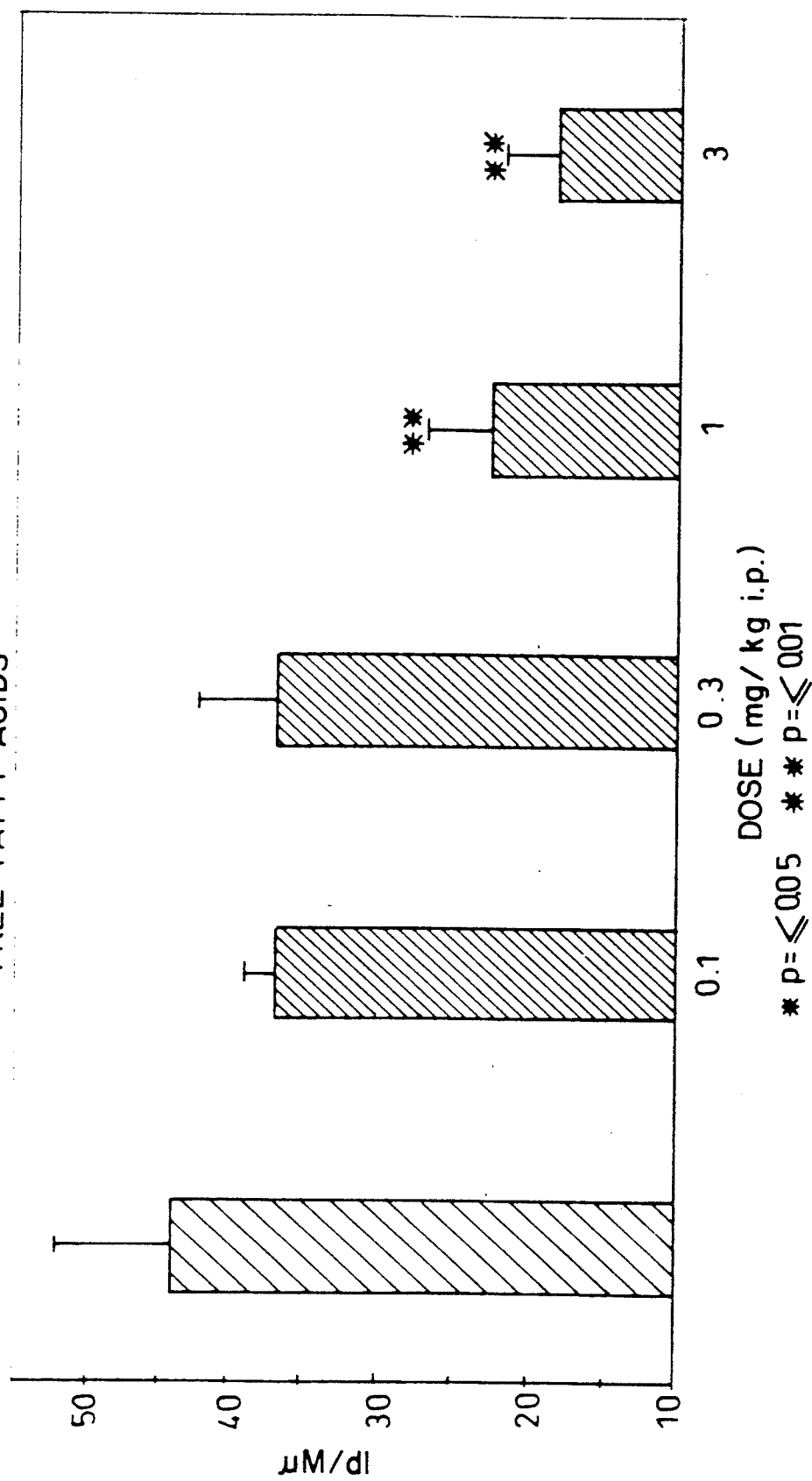

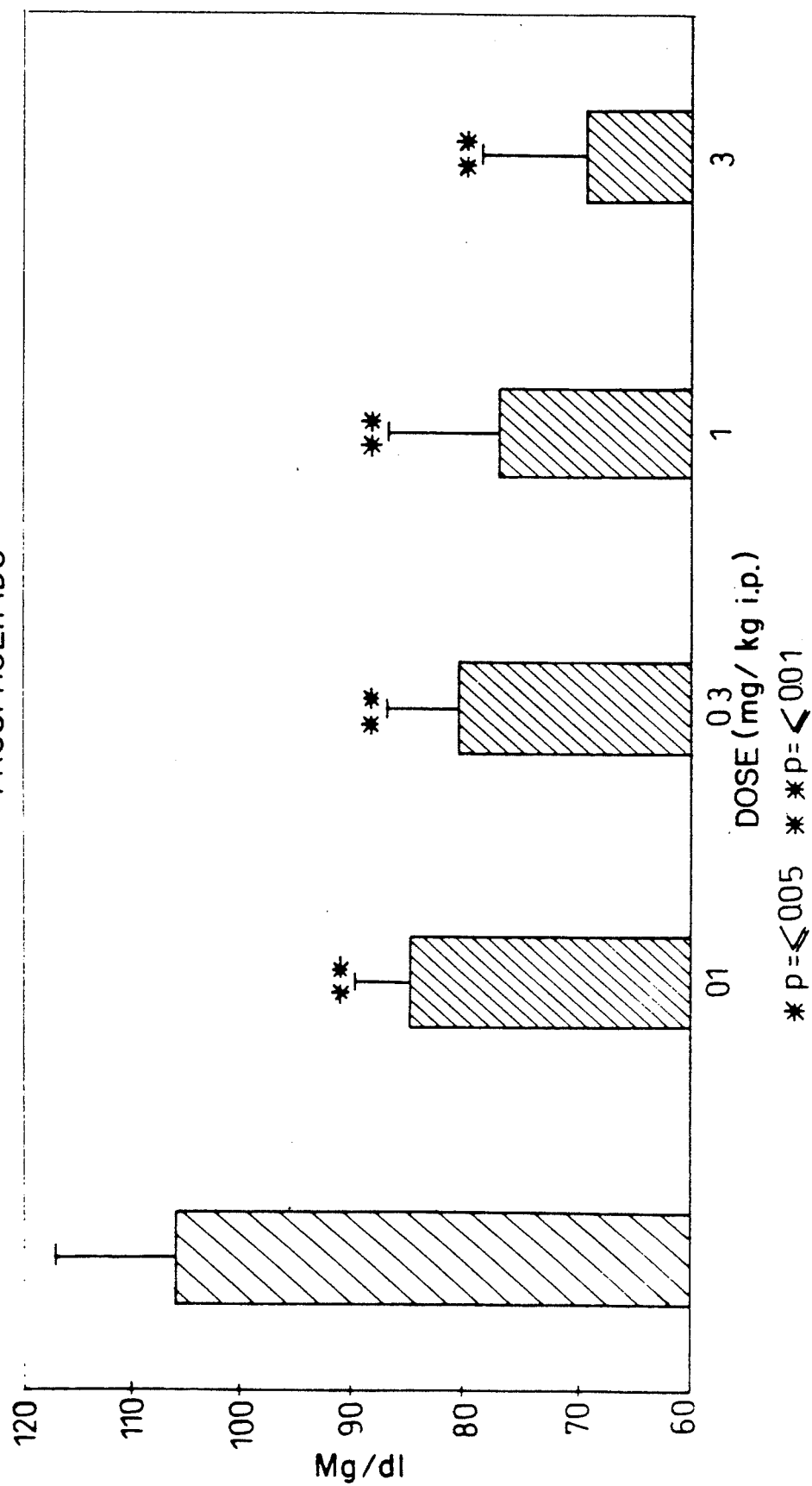

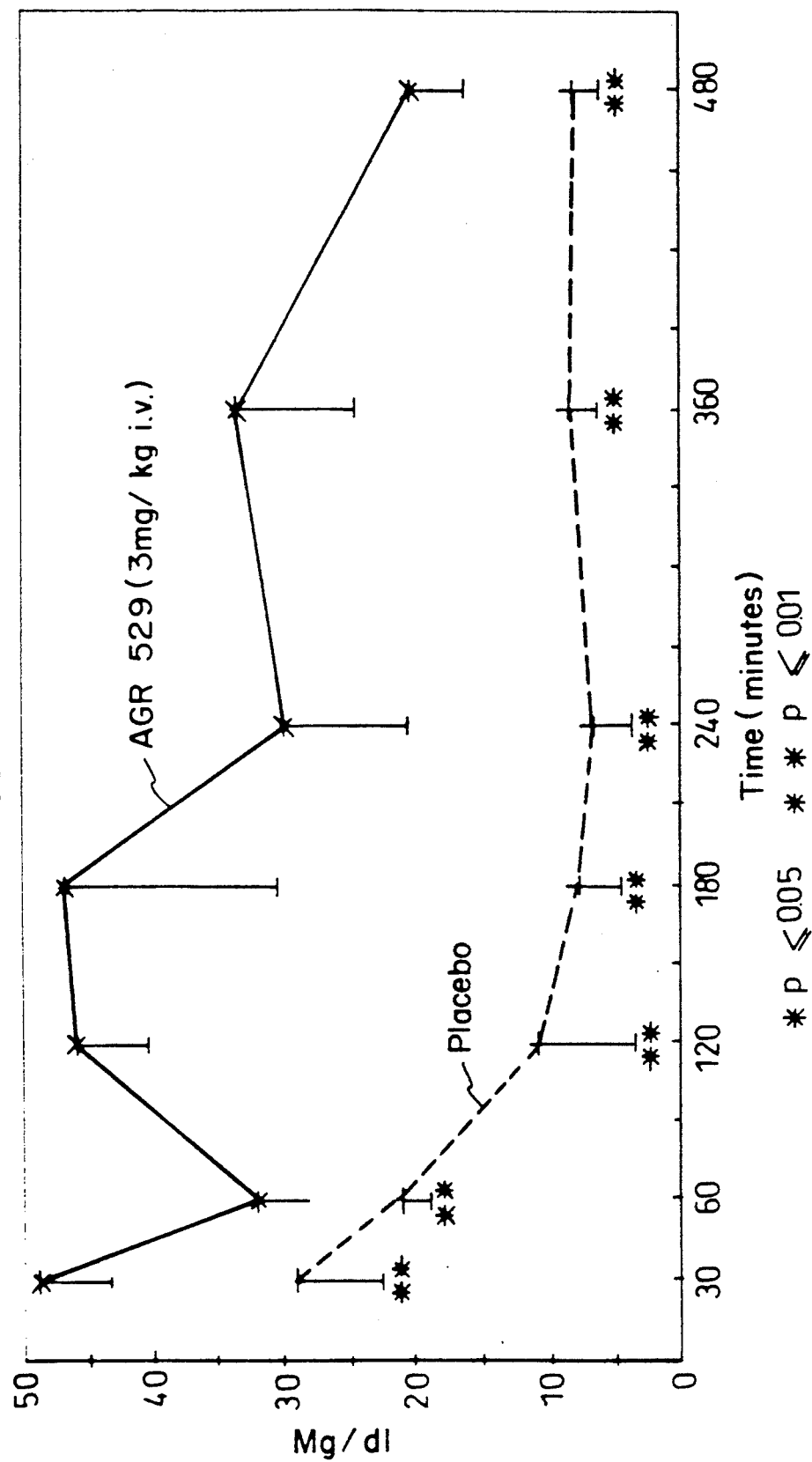

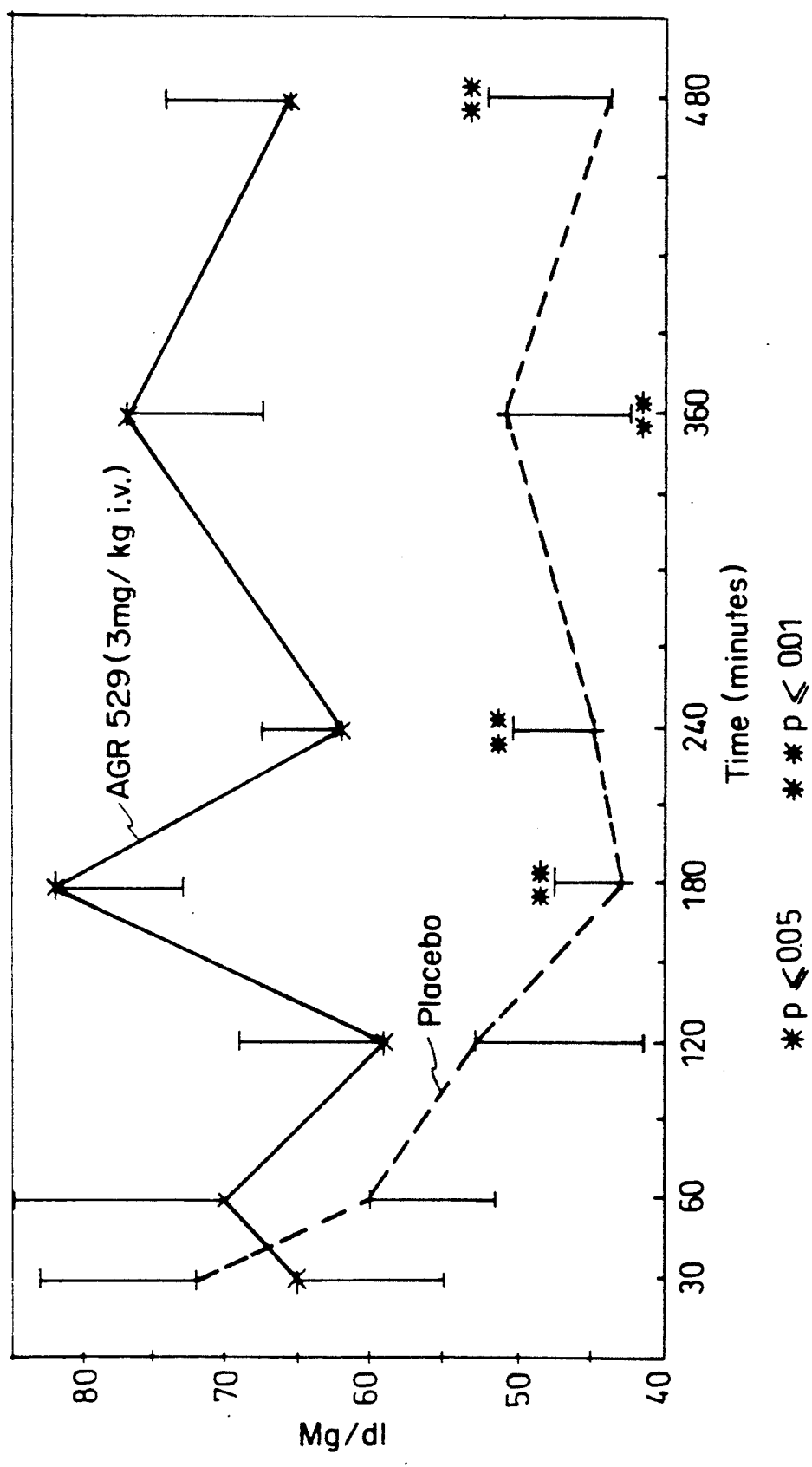

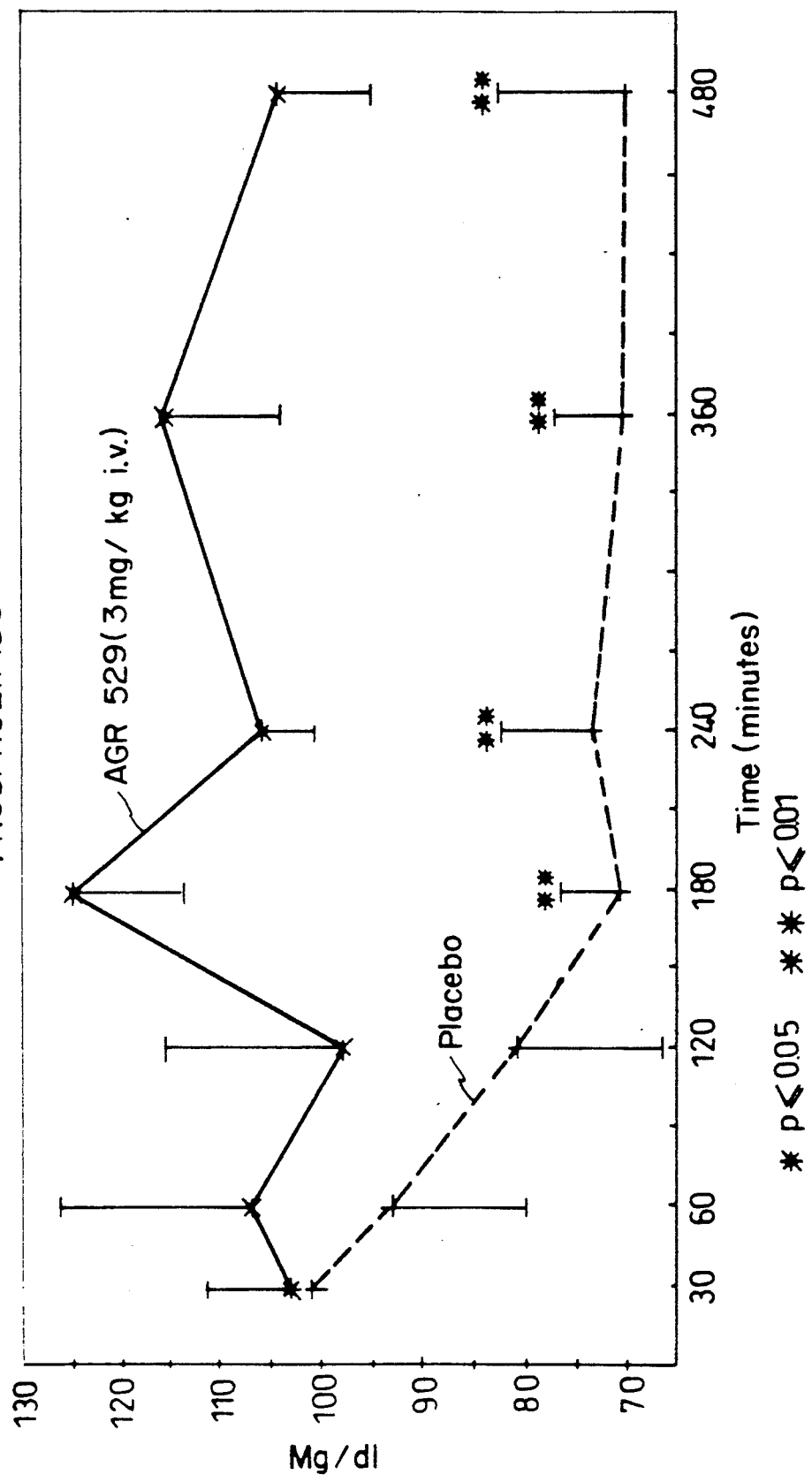

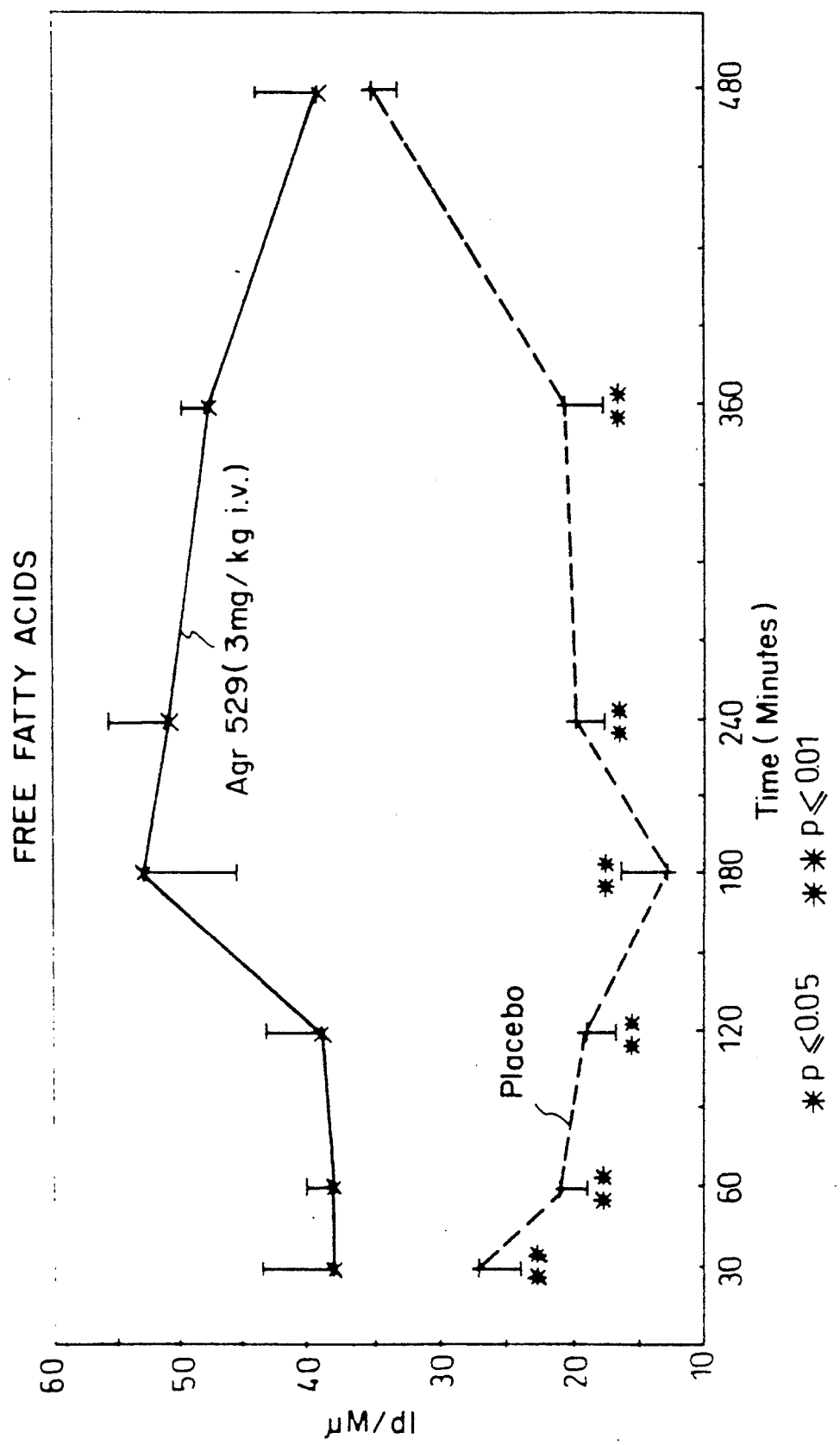

TREATMENT OF HYPERLIPEMIA AND HYPERTRIGLYCERIDEMIA

This is a continuation of Ser. No. 07/739,860, filed Aug. 2, 1991, now abandoned.

The present invention relates to the application of a substance which contains, as active principle, an adenosine substituted on $N^6$, in order to obtain a medicament intended for the treatment of hyperlipemia and hypertriglyceridemia.

French Patent A-8419047 describes a particularly strong hypotensive or anti-hypertensive, anti-inflammatory and analgesic action of a substituted adenosine of formula I

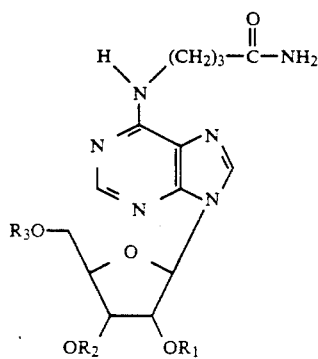

in which $R_1$, $R_2$ and $R_3$ each represent hydrogen (Agr 529) or

Now it has been found that the administration of Agr 529 ($N_6$-3-carboxamido-propyl) adenosine and of its pro-drug Agr 540 [6-(3-carboxamido-propylamino)-9-(2', 3', 5', tripropionyl-$\beta$-D-ribosyl) purine] produces in normal animals a hypolipemia (reduction of fatty acids, phospholipides, triglycerides and cholesterol) and results in a normalizing of the hypertriglyceridemia provoked.

The invention therefore proposes the application of Agr 529 and Agr 540 as active ingredient for the obtaining of a medicament intended for the treatment of hyperlipemia and hypertriglyceridemia.

The experiments have therefore related, on the one hand, to animals on which a hypertriglyceridemia has been provoked and, on the other hand, to normal animals.

BRIEF DESCRIPTION OF THE DRAWINGS

FIGS. 1-6 present date obtained from the use of compound Agr 529 intraperitioneally.

FIGS. 5-8 present data obtained from the use of compound Agr 529 intravenously.

Figure 1:
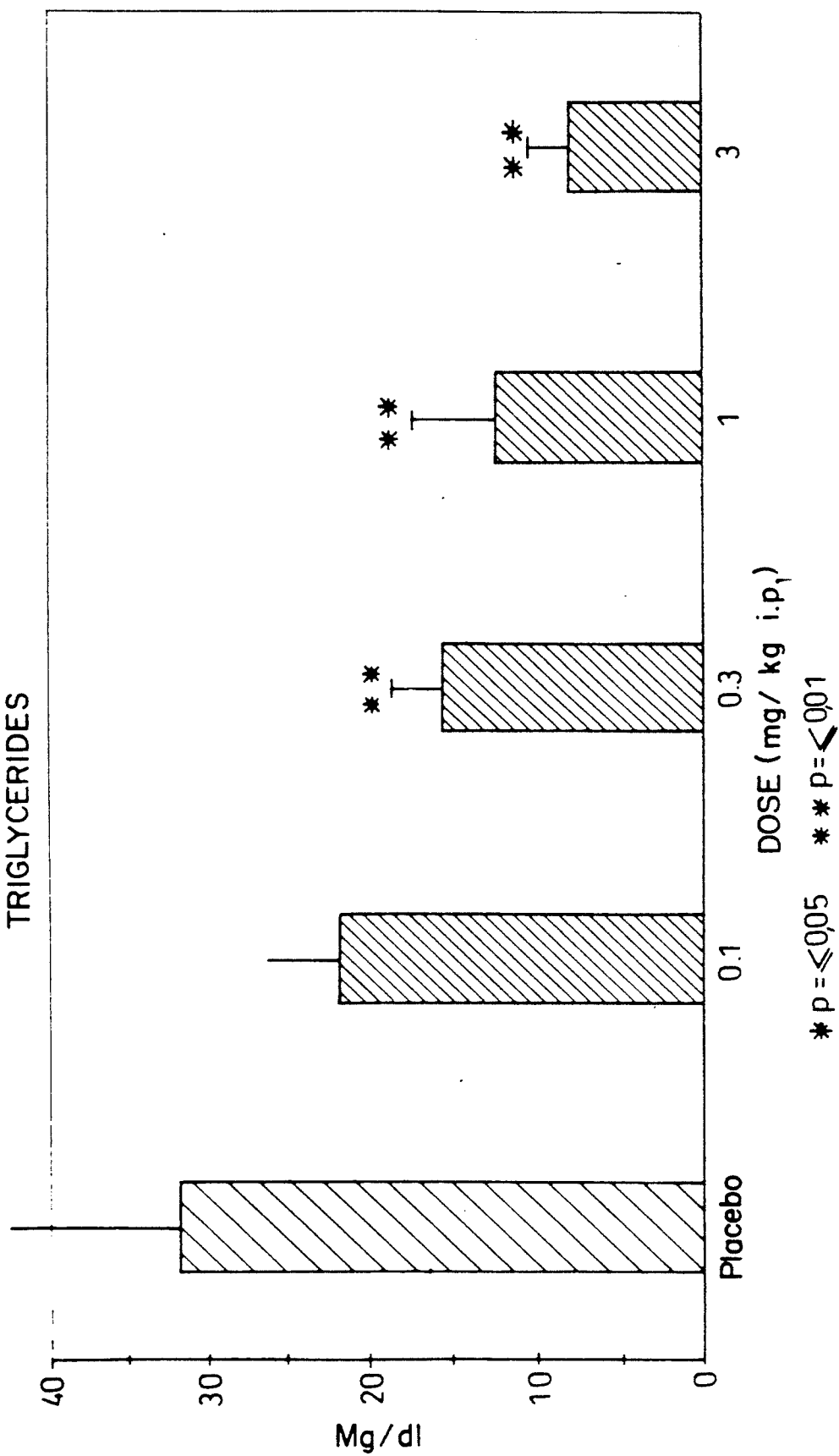
Figure 2:
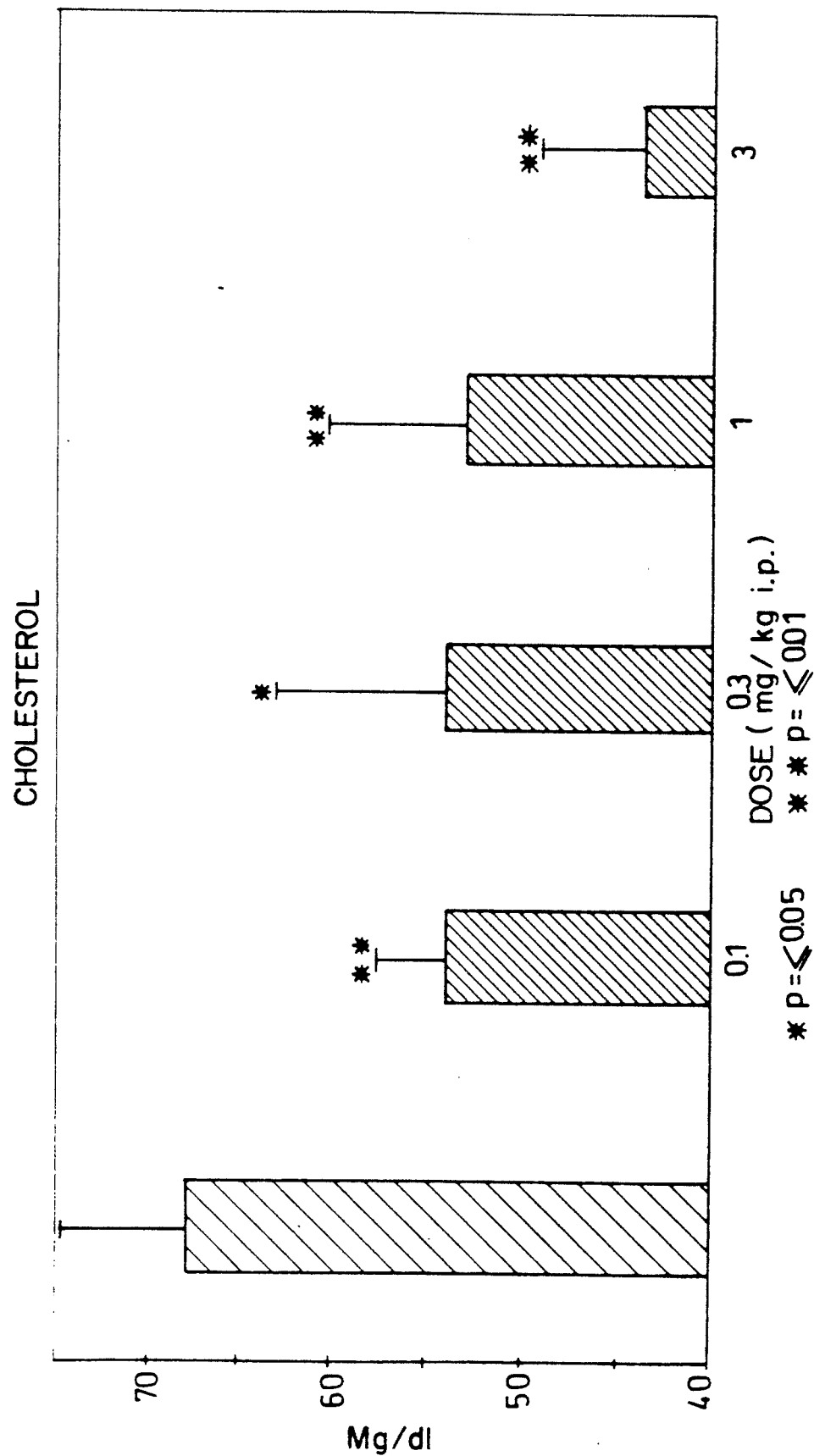

TEST FOR PROVOKED HYPERTRIGLYCERIDEMIA.

The experiment relates to the following two types of animals:
Fauve de Bourgogne rabbits of an average weight of 2 kg (EGAV).
Sprague-Dawley male white rats, Iffa Credo, of an average weight of 260-270 g.

The hypertriglyceridemia is obtained by the intravenous (iv) injection of Triton WR1339 (tyloxapol) in a dose of 600 mg/kg, obtained from the Sigma Chemical Company, N. T 8761 (marginal vein of the ear of the rabbit, jugular vein or vein of the penis of the rat, under slight ether anesthesia, the pentobarbital which attaches itself on the A1 receptors being capable of interacting with the molecules used (Lhose et al., 1985). All the animals used had fasted for 15 hours. The blood was collected over heparin, centrifuged for 20 minutes (3000 rpm at 4° C.). In the serum collected, the TG (triglycerides) are determined in accordance with the GPO-PAP method Boeringher Peridochrom ® Kit, item 701-882.

In normal animals, the fatty acids, triglycerides and cholesterol are determined by automated enzymatic reactions.

1. Experiments on rabbits

The animals are divided into two lots:
a control lot (6 animals) receiving isotonic saline solution iv in a volume of 0.5 ml/kg two hours before the injection of Triton and the same dose of saline solution as previously.
a treated lot (7 animals) receiving 2 mg/kg of Agr 529 iv in a volume of 0.5 ml/kg two hours before the injection of Triton and a new dose of Agr 529 (2 mg/kg).

A sampling of arterial blood, two hours after the injection of the Triton, permits determination of the triglycerides.

2. Experiment by intraperitoneal route on rats

The animals are divided into two lots:
a control lot (4 animals) receiving isotonic saline solution in a volume of 0.2 ml/100 g of rat by intraperitoneal injection (ip), 20 minutes before the injection of the Triton (iv).
a treated lot (5 animals) receiving 2 mg/kg of Agr 529 ip, under the same conditions as the controls.

Two hours later, the animals are sacrificed by decapitation; the blood is collected by the method previously described, for determination of the triglycerides.

3. Experiment per os on rats

The animals are divided into six lots:
one control-control lot receiving per os isotonic saline solution in a volume of 0.2 ml/100 g of rat 30 minutes before the iv injection of isotonic saline solution.
a Triton control lot receiving per os isotonic saline solution 30 minutes before the iv injection of Triton.
an Agr 529 lot (3 mg/kg in a volume of 0.2 ml/100 g of rat), 30 minutes before the iv injection of Triton.
one lot receiving, under the same conditions, 30 mg/kg of Agr 529 per os.
two lots receiving, under the same conditions as previously, 3 and 30 mg/kg of Agr 540 per os.

EXPERIMENTS ON NORMAL ANIMALS

1. Intravenous administration

The animals are distributed into six lots of five animals each:
a control lot receiving the placebo (0.9% isotonic saline solution), five treated lots receiving 0.03, 0.1, 0.3, 1 and 3 mg/kg of Agr 529 respectively by intravenous injection.

The animals are sacrificed two hours after the injection of the product.

2. Intraperitoneal administration

The animals are distributed in five lots of five animals each:

one control lot.

four treated lots receiving 0.1, 0.3, and 3 mg/kg.

The animals are sacrificed two hours after the administration of the Agr 529.

3. Significance

The statistical study is carried out by means of the student t test with * $P<0.05$;  $P<0.01$; * $P<0.001$ or by the Dunnett test with * $P<0.05$ and ** $P<0.01$.

RESULTS

A. Provoked Hypertriglyceridemia

1. In rabbits by intravenous injection

In the control animals, Triton causes a significant increase (***) of the triglycerides of 196.5%, while in the animals which previously received Agr 529 (2 mg/kg iv), the increase is 45% (*). Compared with the Triton controls and at the time 4, the animals which received the Agr 529 have a concentration of triglycerides 150% less than the controls (see Table I).

2 In rats a) Agr 529 by intraperitoneal injection

The ip injection of Agr 529 causes a decrease of 54% in the quantity of triglycerides in circulation. This action of the Agr 529 is significant (**) (see Table II).

b) Agr 529 with administration per os.

Per os, Agr 529 and Agr 540 significantly oppose the increase in the circulating triglycerides. The greatest action is obtained with 30 mg/kg (51% inhibition; see Table III). It will be noted that the action of the Agr 529 is substantially the same as that of the Agr 540, despite the fact that the latter is better absorbed per os (report submitted on Agr 529). This is undoubtedly due to the fact that small (nanomolar) doses are sufficient for the action on the A1 receptors. One can contemplate using smaller doses of the two compounds in the model developed, since the action obtained is not significantly changed by increasing the dose from 30 mg/kg, at least with respect to the Agr 529.

B. NORMAL RATS a) Agr 529, intravenous

Within the range of the doses used, the hypolipemizing effect appears only as from 0.1 mg/kg. At 3 mg/kg, a significant decrease is noted, two hours after the injection, in the concentration of plasma triglycerides, total cholesterol, fatty acids and phospholipids.

b) Agr 529, Intraperitoneal

The same actions are found as upon iv route, but the hypolipemizing effect starts to be significant only as from 0.3 mg/kg (FIGS. I, II, III, IV).

c) Kinetic study of Agr 529 in an amount of 3 mg/kg iv (FIG. V, VI, VII, VIII).

The administration of 3 mg/kg of Agr 529 results in a significant decrease in the concentrations of fatty acids, triglycerides, total cholesterol and phospholipids. The effect starts to appear 30 minutes after the injection and increases in time. The decrease is maximum at the end of two hours. Eight hours after the administration, there is a tendency to return to the base values. This indicates that the action of Agr 529 is of long duration and that it is not destroyed by the adenosine deaminase.

Summarizing, employing a model of hypertriglyceridemia provoked by the intravenous injection of Triton WR 1339, it has been found that Agr 529 [N(3-amino-propyl-adenosine) hydrochloride] in an amount of 2 mg/kg intravenously in rabbits on the one hand, and intraperitonealy on the other hand, normalized the plasma concentration of the circulating triglycerides.

Furthermore, Agr 529 and its pro-drug Agr 540 [6-(3-carboxamido-propylamino)-9-(2',3', 5'tripropionyl)-β, D-ribosyl)-purine][administered per os in doses of 3 and 30 mg/kg in rats return the triglycerides plasma concentrations to normal.

The intravenous administration of Agr 529 to normal rats causes a decrease, as a function of the doses, of the plasma concentrations of fatty acids, phospholipides, triglycerides and total cholesterol. The decrease commences at a dose of 0.1 mg/kg and becomes highly significant at 3 mg/kg, at which dose a hyperglycemia is furthermore noted. Under the same conditions, the intraperitoneal administration of Agr 529 also results in a hypolipemia as a function of the doses. However, at 0.3 mg/kg, hyperglycemia is no longer found. No action is to be noted on the cholesterol and triglyceride concentrations of the high density lipoproteins (HDL).

A kinetic study shows that the hypolipemizing action of Agr 529 at 3 mg/kg upon intravenous injection manifests itself 30 minutes after the injection, with a maximum effect at two hours. The effect persists for eight hours after the injection.

An in vitro study on microsomal fraction of liver shows that Agr 529 has no action on the activity of the HMG CoA reductase (β-hydroxy-β-methylglutaryl CoA reductase; key enzyme of the synthesis of cholesterol). The same is true with regard to the activity of ACAT (cholesterol-O-acyl transferase), the esterification enzyme of cholesterol.

In conclusion, it is shown that the administration of Agr 529 and Agr 540 in normal animals causes a hypolipemia (reduction of fatty acids, phospholipides, triglycerides and cholesterol) and results in a normalizing of the provoked hypertriglyceridemia.

The active doses for observing the effects which are the object of the present application are smaller by several factors than those which produce the effects which form the object of French Patent 84 19 047. The latter have not been observed or as negligible in the hypolipemizing doses.

TABLE I

Action of Agr 529 in a dose of 2 mg/kg, administered intravenously (iv), on the hypertriglyceridemia provoked by the injection by the same route of 600 mg/kg of Triton in Fauve de Bourgogne rabbits (n = number of animals).

| Animals | Triglycerides mmol/liter time = 0 | Product injected | Latency (hours) | Triglycerides mmol/liter time = 2 | Product injected | Latency (hours) | Triglycerides mmol/liter time = 4 |
|---|---|---|---|---|---|---|---|
| Controls n = 6 | 1.74 ± 0.16 | Solvent NaCl 0.9% iv | 2 | 2.98 ± 0.40 | Solvent NaCl 0.9%, iv + Triton 600 mg/kg iv | 2 | 8.83 ± 1.13 |
| | | | | | | | ←——————→ +196.5%*** |
| Test n = 7 | 1.95 ± 0.34 | Agr 529 2 mg/kg iv | 2 | 3.19 ± 0.38 | Agr 529 2 mg/kg iv + Triton 600 mg/kg iv | 2 | 4.65 ± 0.44 |
| | | | | | | | ←——————→ +45%** |

TABLE II

Action of Agr 529 (2 mg/kg) ip on the hypertriglyceridemia provoked by the intravenous injection of 600 mg/kg of Triton in rats (n = number of animals).

| | Animals | |
|---|---|---|
| | Controls 0.9% NaCl solution + Triton 600 mg/kg | Tests Agr 529 2 mg/kg + Triton 600 mg/kg |
| Dose | n = 4 | n = 5 |
| Triglycerides mmols/liter | 6.32 ± 0.92 | 2.90 ± 0.26 |
| | ←————→ −54%** | |

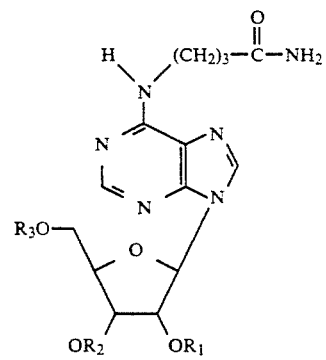

(I)

TABLE III

Action of Agr 529 in doses of 3 and 30 mg/kg per os and of Agr 540 in doses of 3 and 30 mg/kg per os on the hypertriglyceridemia provoked by the intravenous injection of 600 mg/kg of Triton in rats (n = number of animals).

| Dose | Controls NaCl 0.9% n = 8 | Controls Triton 600 mg/kg n = 13 | Tests Agr 529 3 mg/kg P.O. + Triton 600 mg/kg iv n = 4 | Tests Agr 529 30 mg/kg P.O. + Triton 600 mg/kg iv n = 5 | Tests Agr 540 30 mg/kg P.O. + Triton 600 mg/kg iv n = 6 | Tests Agr 540 30 mg/kg P.O. + Triton 600 mg/kg iv n = 8 |
|---|---|---|---|---|---|---|
| Triglycerides mmols/liter | 0.52 ± 0.10 | 7.53 ± 0.49 | 4.87 ± 0.69 | 4.64 ± 0.74 | 5.65 ± 0.46 | 3.67 ± 0.59 |
| | | ←——→ −35%** | | | | |
| | | ←————→ −38%** | | | | |
| | | ←——————→ −25%* | | | | |
| | | ←————————→ −51%** | | | | |

We claim:

1. A method of treatment of hyperlipemia for a host in need thereof, which comprises administering to said host an effective amount of an adenosine substituted on $N^6$ of formula I in which $R_1$, $R_2$ and $R_3$ each represents hydrogen or

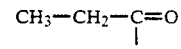

2. A method according to claim 1, in which $R_1$, $R_2$, $R_3$ each represents hydrogen.

3. A method according to claim 1, in which $R_1$, $R_2$, $R_3$ each represents the

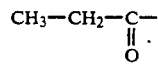

radical.

4. A method of treatment of hypertriglyceridemia for a host in need thereof, which comprises administering to said host an effective amount of an adenosine substituted on $N^6$ of formula I

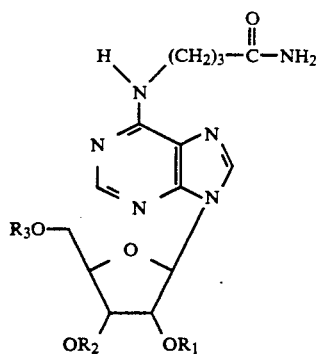

in which $R_1$, $R_2$ and $R_3$ each represent hydrogen or

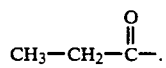

5. A method according to claim 4, in which $R_1$, $R_2$ and $R_3$ each represents hydrogen.

6. A method according to claim 4, in which $R_1$, $R_2$ and $R_3$ each represents the

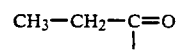

radical.

* * * * *